United States Patent [19]
Kirkpatrick

[11] 4,082,765
[45] Apr. 4, 1978

[54] COMBATING INSECTS AND MITES WITH 1-CARBAMYL-4H-1,2,4-TRIAZOLIN-5-ONES AND THIONES

[75] Inventor: Joel L. Kirkpatrick, Overland Park, Kans.

[73] Assignee: Gulf Research & Development Co., Pittsburgh, Pa.

[21] Appl. No.: 796,947

[22] Filed: May 16, 1977

Related U.S. Application Data

[60] Division of Ser. No. 660,090, Feb. 23, 1976, which is a continuation-in-part of Ser. No. 508,476, Sep. 23, 1974, abandoned, which is a continuation-in-part of Ser. No. 295,318, Oct. 5, 1972, abandoned.

[51] Int. Cl.$^2$ .................. A01N 9/12; A01N 9/22; C07D 249/12; C07D 401/04
[52] U.S. Cl. .................. 260/308 C; 260/294.8 H; 424/263; 424/269
[58] Field of Search .................. 260/308 C, 308 R

[56] References Cited

U.S. PATENT DOCUMENTS

| | | | |
|---|---|---|---|
| 3,308,131 | 3/1967 | McKusick | 260/308 R |
| 3,376,306 | 4/1968 | Roland | 260/294 |
| 3,808,334 | 4/1974 | Dahle | 260/308 B |
| 3,824,312 | 7/1974 | Seidel et al. | 260/308 R |
| 3,952,001 | 4/1976 | Brookes | 260/308 R |

*Primary Examiner*—Alton D. Rollins
*Attorney, Agent, or Firm*—Carl A. Cline

[57] ABSTRACT

Insects and mites are combated by applying to the locus of insects in at least one stage of the insects' life cycle an effective amount of a compound having the structural formula

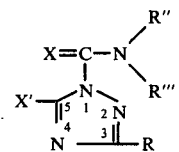

in which X and X' may be oxygen or sulfur, R may be alkyl, cycloalkyl, aryl, alkenyl, alkynyl, optionally substituted with halogen, hydroxy, alkoxy, nitro, mercapto or alkylthio substituents, R' may be hydrogen, alkyl, cycloalkyl, alkenyl, alkynyl, aryl etc., and if R' is not hydrogen one of R" and R'" may be hydrogen while one or both may be alkyl, optionally substituted with halogen, hydroxy, alkoxy, mercapto or alkylthio substituents or R" and R'" together may be part of a heterocyclic ring containing 2 to 6 carbon atoms, with the provision that the total of R, R', R" and R'", must contain from 4 to 9 carbon atoms and if R is straight chain alkyl having less than 6 carbon atoms, none of R', R" and R'" may be hydrogen. The novel insecticides are particularly useful in combating aphids.

36 Claims, No Drawings

COMBATING INSECTS AND MITES WITH 1-CARBAMYL-4H-1,2,4-TRIAZOLIN-5-ONES AND THIONES

This is a division of U.S. Ser. No. 660,090, filed Feb. 23, 1976, which is a continuation-in-part of U.S. patent application Ser. No. 508,476 filed Sept. 23, 1974, now abandoned, which is a continuation-in-part of U.S. patent application Ser. No. 295,318, filed Oct. 5, 1972, now abandoned.

DESCRIPTION OF THE INVENTION

I have discovered that insects and mites may be combated effectively by a class of 1,2,4-triazoline compounds which have not previously been used for this purpose. Insect pests and particularly aphids are combated by applying to the locus of the insects in at least one stage of the insects' life cycle an effective amount of a compound having the structural formula $$\begin{array}{c} X=C-N \diagup R'' \\ | \phantom{X=}\diagdown R''' \\ X'=\underset{|}{\overset{N}{\underset{4}{\overline{\phantom{XX}}}}}\overset{1}{\underset{3}{\phantom{X}}}\overset{\diagdown}{\underset{\phantom{X}}{N}}\phantom{X}R''' \\ R'-N \underset{\phantom{XX}}{\overline{\phantom{XXXX}}}R \end{array}$$

in which X and X' may be oxygen or sulfur, R may be alkyl, cycloalkyl, aryl, alkenyl, alkynyl, optionally substituted with halogen, hydroxy, alkoxy, nitro, mercapto or alkylthio substituents, R' may be hydrogen, alkyl, cycloalkyl, alkenyl, alkynyl, aryl, aralkyl, and if R' is not hydrogen one of R" and R''' may be hydrogen while one or both may be alkyl, optionally substituted with halogen, hydroxy alkoxy, mercapto or alkylthio substituents or R" and R''' together may be part of a heterocyclic ring containing 2 to 6 carbon atoms, with the provision that the total of R, R', R"and R''' must contain from 4 to 9 carbon atoms and if R is straight chain alkyl having less than 6 carbon atoms, none of R', R" and R''' may be hydrogen. Preferably, either or both R" and R" are methyl.

SYNTHESIS OF THE INSECTICIDES

The insecticidal compounds may be synthesized by general procedures, employing commercially available intermediate compounds. The products are highly toxic substances, requiring suitable precautionary measures so as to avoid contact during handling.

The following specific procedures are presented by way of illustration:

Preparation of 3-t-butyl-4-methyl-4H-1,2,4-triazoline-5-thione

To a suspension of 44 g (0.42m) of 4-methyl-thiosemicarbazide and 35 g 0.45m) of pyridine in 300 ml of dioxane was added 50 g (0.41m) of pivaloyl chloride, with cooling. The reaction was heated at reflux for 3 hrs., cooled and poured into ice water. The resulting solid was collected, washed with water and air dried. The crude 1-pivaloyl-4-methylthiosemicarbazide was dissolved in 300 ml of 10% NaOH and heated at reflux for 3 hours. After cooling, the pH was adjusted to 6 with acetic acid and the resulting precipitate was collected, washed with water and dried, giving 40 g, MP 162°–165° (57%). An analytical sample was obtained from methanol-chloroform, MP 165°–166°.

Preparation of 1-(N,N-Dimethylcarbamyl)-3-t-butyl-4-methyl-4H-1,2,4-triazoline-5thione Dimethylcarbamyl chloride (21.6g, 0.2m) was added to a solution of 17.1 g (0.1m) of 3-t-butyl-4-methyl-4H-1,2,4-triazoline-5-thione in 300 ml of anhydrous pyridine and heated at reflux for 16 hours. The pyridine was removed on a rotary evaporator, water was added and, after cooling, 23.2g (95%) of 1-(N,N-dimethylcarbamyl)-3-t-butyl-4-methyl-4H-1,2,4-triazoline-5-thione, MP 159°–161°, was collected. Recrystallization from methylene chloride-petroleum ether gave the analytical sample, MP 160°–161°. Compounds which have been made by this general technique include those listed by substituents and melting points in the following table.

$$\begin{array}{c} X=C-N \diagup R'' \\ | \phantom{X=}\diagdown R''' \\ S=\underset{|}{\overset{N}{\phantom{X}}}\overset{\diagdown}{\underset{\phantom{X}}{N}}\phantom{X}R''' \\ R'-N \underset{\phantom{XX}}{\overline{\phantom{XXXX}}}R \end{array}$$

| COMPOUND NO. | R | R' | R" | X | R''' | M.P. (° C) |
|---|---|---|---|---|---|---|
| 1 | t-Butyl | —CH$_3$ | H | O | —CH$_3$ | 117–118° |
| 2 | 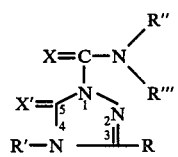 | —CH$_3$ | —CH$_3$ | O | —CH$_3$ | 150–151° |
| 3 | Cl—⌬ | —CH$_2$CH$_3$ | —CH$_3$ | O | —CH$_3$ | 125–126° |
| 4 | CH$_3$ | —CH$_3$ | —CH$_3$ | O | —CH$_3$ | 140–141° |
| 5 | CH$_3$ | —CH$_3$ | H | O | —CH$_3$ | 152–156 |
| 6 | Butyl | —CH$_3$ | H | O | —CH$_3$ | 107–108° |
| 7 | Isopropyl | —CH$_3$ | —CH$_3$ | O | —CH$_3$ | 136–138° |
| 8 | t-Butyl | —CH$_3$ | —CH$_2$—CH$_3$ | O | —CH$_2$—CH$_3$ | 81–82° |
| 9 | cyclopropyl | —CH$_3$ | —CH$_3$ | O | —CH$_3$ | 119–121° |
| 10 | H | —CH$_3$ | —CH$_3$ | O | —CH$_3$ | 181–182° |
| 11 | cyclopropyl | —CH$_3$ | H | O | —CH$_3$ | 118–120° |
| 12 | H | —CH$_3$ | H | O | —CH$_3$ | 169–172° |

-continued

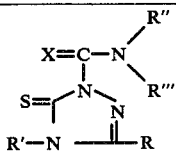

| COMPOUND NO. | R | R' | R'' | X | R''' | M.P. (° C) |
|---|---|---|---|---|---|---|
| 13 | CH$_2$CH$_3$ | —CH$_3$ | —CH$_3$ | O | —CH$_3$ | 114–116° |
| 14 | t-butyl | —CH$_3$ | —CH$_3$ | O | —CH$_3$ | 160–161° |
| 15 |  | —CH$_3$ | —CH$_3$ | O | —CH$_3$ | 140–142° |
| 16 |  | —CH$_3$ | —CH$_3$ | O | —CH$_3$ | 157–159° |
| 17 | t-butyl | CH$_3$CH$_3$— | —CH$_3$ | O | —CH$_3$ | 134–136° |
| 18 | —CF$_3$ | —CH$_3$ | —CH$_3$ | O | —CH$_3$ | 149–150° |
| 19 | CH$_3$CH$_2$ | —CH$_3$ | H | O | —CH$_3$ | 127–129° |
| 20 | CH$_3$CH$_2$—CH$_2$— | —CH$_3$ | H | O | —CH$_3$ | 113–115° |
| 21 | t-butyl | CH$_3$CH$_2$ | H | O | —CH$_3$ | 104–107° |
| 22 | isobutyl | —CH$_3$ | —CH$_3$ | O | —CH$_3$ | 142–144° |
| 23 | neopentyl | —CH$_3$ | —CH$_3$ | O | —CH$_3$ | 128–130° |
| 24 | t-butyl | —CH$_3$ | —CH$_3$ | S | —CH$_3$ | 157–159° |
| 25 | cyclohexyl | —CH$_3$ | —CH$_3$ | O | —CH$_3$ | 145–147° |
| 26 | propenyl | —CH$_3$ | —CH$_3$ | O | —CH$_3$ | 144–147° |
| 27 | cyclohexyl | CH$_3$— | —CH$_3$ | O | —CH$_3$ | 145–147° |
| 28 | (CH$_3$)$_3$C— | phenyl | —CH$_3$ | O | —CH$_3$ | 223–225° |
| 29 | (CH$_3$)$_3$C— | benzyl | —CH$_3$ | O | —CH$_3$ | 133–134° |
| 30 | N≡C—CH$_2$— | —CH$_3$ | —CH$_3$ | O | —CH$_3$ | 174–176° |
| 31 | (CH$_3$)$_3$C— | CH$_3$—(CH$_2$)$_2$—CH$_2$— | —CH$_3$ | O | —CH$_3$ | 90–91° |
| 32 | (CH$_3$)$_3$C— | CH$_2$=CH—CH$_2$— | —CH$_3$ | O | —CH$_3$ | 127–129° |
| 33 | —CF$_3$ | CH$_3$CH$_2$— | —CH$_3$ | O | —CH$_3$ | 93–94° |
| 34 | —CF$_3$ | CH$_2$=CH—CH$_2$— | —CH$_3$ | O | —CH$_3$ | 85–88° |
| 35 | —CF$_3$ | CH$_3$(CH$_2$)$_2$—CH$_2$— | —CH$_3$ | O | —CH$_3$ | liquid |
| 36 | p-nitrophenyl | CH$_3$— | —CH$_3$ | O | —CH$_3$ | 234–236° |

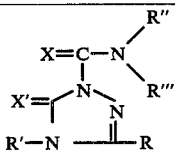

| COMPOUND NO. | R | R' | R'' | X | R''' | X' | M.P. (° C) |
|---|---|---|---|---|---|---|---|
| 37 | —CH$_2$—N(CH$_3$)$_2$ | CH$_3$— | —CH$_3$ | O | —CH$_3$ | S | 99–100° |
| 38 | —CClF$_2$ | CH$_3$— | —CH$_3$ | O | —CH$_3$ | S | liquid |
| 39 | —C(CH$_3$)$_2$—CH$_2$CH$_3$ | CH$_3$— | —CH$_3$ | O | —CH$_3$ | S | 95–96° |
| 40 | —C(CH$_3$)$_2$—S—CH$_3$ | CH$_3$— | —CH$_3$ | O | —CH$_3$ | S | 92–94° |
| 41 | —S—CH(CH$_3$)$_2$ | CH$_3$— | —CH$_3$ | O | —CH$_3$ | S | 64–65° |
| 42 | —S—CH$_2$CH$_3$ | CH$_3$— | —CH$_3$ | O | —CH$_3$ | S | 88–89° |
| 43 | —C(CH$_3$)$_2$—CH$_2$CH$_3$ | CH$_3$— | —H | O | —CH$_3$ | S | 88–90° |
| 44 | —S—CH(CH$_3$)$_2$ | CH$_3$— | —CH$_3$ | O | —CH$_3$ | O | liquid |
| 45 | —S—CH$_2$CH$_3$ | CH$_3$— | —CH$_3$ | O | —CH$_3$ | O | 73–74 |
| 46 | —SCH$_3$ | CH$_3$— | —CH$_3$ | O | —CH$_3$ | O | 115–117° |
| 47 | —SCH$_3$ | CH$_3$— | —CH$_3$ | O | —CH$_3$ | O | liquid |
| 48 | —CH$_2$N(C$_2$H$_5$)$_2$ | CH$_3$— | —CH$_3$ | O | —CH$_3$ | S | $N_D^{20}$ = 1.5347 |
| 49 | —SCH$_2$CH$_3$ | CH$_3$— | —CH$_3$ | O | —CH$_3$ | S | $N_D^{27}$ = 1.5666 |
| 50 | —SCH$_2$CH=CH$_2$ | CH$_3$— | —CH$_3$ | O | —CH$_3$ | S | liquid |
| 51 | —CH(C$_2$H$_5$)—CH$_3$ | CH$_3$— | —CH$_3$ | O | —CH$_3$ | S | 76–78° |
| 52 | —CH$_2$—SO$_2$—CH$_3$ | CH$_3$— | —CH$_3$ | O | —CH$_3$ | S | 164–165° |

Combating Insects and Mites

The combating of insects and mites may be demonstrated by the procedure described below.

Each chemical compound is formulated at 500 ppm concentration by dissolving 25 mg of the compound in 5 ml of Acetone, adding to the resulting solution in a 50 ml. volumetric flask sufficient 0.12 percent aqueous solution of octylphenoxy polyoxyethanol surfactant to bring the volume up to the mark and mixing by shaking. Lower concentrations are obtained by dilution with water.

Method for Mites, Aphids, Bean Beetles and Army Worms

Three 5 oz paper cups containing Henderson dwarf lima bean plants and one 5 oz paper cup containing Orange Gem Nasturtiums, all growing in vermiculite, are placed on a turntable and sprayed to thorough wetness with 25 ml of a solution of the candidate chemical at the appropriate concentration. Nasturtiums were already infested with 50–100 bean aphids (BA). A bean plant in one paper cup was already infested with 50–100 two-spotted mites (TSM). Leaves from the two remaining bean plants are removed following spraying and placed in disposable petri dishes with 5 southern armyworm (SA) larvae in one petri dish, and 5 Mexican bean beetle (MBB) larvae in the other petri dish. The rating is done approximately 48 hours after spraying as follows:

| RESULT | RATING |
| --- | --- |
| None dead | 0 |
| 1-25% dead | 1 |
| 26-50% dead | 2 |
| 51-75% dead | 3 |
| 76-99+% dead | 4 |
| 100% dead | 5 |

Results of tests performed on a group of the compounds at a concentration of 500 ppm appear in the following table:

| COMPOUND NO. | MBB | SA | BA | TSM |
| --- | --- | --- | --- | --- |
| 1 | 1 | 0 | 5 | 0 |
| 2 | 0 | 0 | 4 | 0 |
| 3 | 0 | 0 | 3 | 0 |
| 4 | 0 | 0 | 3 | 5 |
| 5 | 0 | 0 | 0 | 0 |
| 6 | 0 | 0 | 0 | 0 |
| 7 | 5 | 5 | 5 | 5 |
| 8 | 3 | 0 | 5 | 0 |
| 9 | 5 | 0 | 4 | 5 |
| 10 | 0 | 0 | 5 | 0 |
| 11 | 0 | 0 | 5 | 0 |
| 12 | 0 | 0 | 1 | 0 |
| 13 | 4 | 0 | 5 | 4 |
| 14 | 5 | 5 | 5 | 5 |
| 15 | 3 | 0 | 4 | 0 |
| 16 | 0 | 0 | 3 | 0 |
| 17 | 5 | 5 | 5 | 5 |
| 18 | 5 | 0 | 5 | 5 |
| 19 | 0 | 0 | 2 | 0 |
| 20 | 0 | 0 | 4 | 0 |
| 21 | 3 | 0 | 4 | 0 |
| 22 | 5 | 0 | 4 | 5 |
| 23 | 3 | 0 | 3 | 0 |
| 24 | 4 | 0 | 4 | 1 |
| 25 | 1 | — | 4 | 0 |
| 26 | 2 | — | 5 | 0 |

In further tests, compounds were compared with a commercial insecticide at concentrations ranging from 500 down to 15 ppm. Representative results are tabulated below:

| COMPOUND NO. | Species | Conc., ppm | | | | | |
| --- | --- | --- | --- | --- | --- | --- | --- |
| | | 500 | 250 | 125 | 62 | 31 | 15 |
| 14 | Mexican Bean Beetle (MBB) | 5 | 5 | 5 | 5 | 5 | 5 |
| | Southern Army Worm (SA) | 5 | 5 | 4 | 0 | 0 | 0 |
| | Bean Aphid (BA) | 5 | 5 | 5 | 5 | 5 | 4 |
| | Two-Spotted Mite (TSM) | 5 | 5 | 5 | 4 | 2 | 0 |
| 4 | Bean Aphid (BA) | 5 | 5 | 5 | 5 | 5 | 5 |
| | Two-Spotted Mite (TSM) | 0 | 0 | 0 | 0 | 0 | 0 |
| 1 | Bean Aphid (BA) | | 5 | 5 | 4 | 2 | 1 |
| 7 | Mexican Bean Beetle (MBB) | 5 | 5 | 5 | 4 | 2 | 1 |
| | Bean Aphid (BA) | 5 | 5 | 5 | 4 | 4 | |
| | Two-Spotted Mite (TSM) | 5 | 5 | 4 | 3 | 1 | |
| 9 | Mexican Bean Beetle (MBB) | 5 | 4 | 3 | 1 | 0 | |
| | Bean Aphids (BA) | 5 | 5 | 5 | 5 | 5 | |
| | Two-Spotted Mite (TSM) | 4 | 4 | 0 | 0 | 0 | |
| 13 | Mexican Bean Beetle (MBB) | 4 | 3 | 1 | 0 | 0 | |
| | Bean Aphid (BA) | 5 | 5 | 5 | 5 | 5 | |
| | Two-Spotted Mite (TSM) | 1 | 0 | 0 | 0 | 0 | |
| 18 | Mexican Bean Beetle (MBB) | 4 | 5 | 2 | 1 | 0 | |
| | Bean Aphid (BA) | 5 | 5 | 5 | 5 | 4 | |
| | Two-Spotted Mite (TSM) | 3 | 2 | 0 | 0 | 0 | |

-continued

| COMPOUND NO. | Species | Conc., ppm | | | | | |
| --- | --- | --- | --- | --- | --- | --- | --- |
| | | 500 | 250 | 125 | 62 | 31 | 15 |
| Diazinon | Mexican Bean Beetle (MBB) | 5 | 5 | 5 | 5 | 5 | 2 |
| | Southern Army Worm (SA) | 5 | 5 | 5 | 5 | 4 | 3 |
| | Bean Aphid (BA) | 5 | 5 | 5 | 4 | 3 | 2 |
| 27 | Mexican Bean Beetle (MBB) | 1 | 0 | 0 | 0 | 0 | 0 |
| | Bean Aphid (BA) | 4 | 5 | 5 | 4 | 3 | 1 |
| 28 | Mexican Bean Beetle (MBB) | 5 | 4 | 4 | 1 | 0 | 0 |
| | Bean Aphid (BA) | 4 | 5 | 5 | 5 | 4 | 4 |
| 29 | Mexican Bean Beetle (MBB) | 5 | 3 | 2 | 2 | 0 | 0 |
| | Bean Aphid (BA) | 4 | 5 | 5 | 4 | 2 | 2 |
| 30 | Bean Aphid (BA) | 5 | 5 | 5 | 5 | 4 | 4 |
| 31 | Mexican Bean Beetle (MBB) | 3 | 5 | 3 | 1 | 0 | 0 |
| | Bean Aphid (BA) | 5 | 5 | 5 | 5 | 5 | 5 |
| 32 | Mexican Bean Beetle (MBB) | 4 | 5 | 5 | 5 | 4 | 4 |
| | Bean Aphid (BA) | 5 | 5 | 5 | 5 | 5 | 5 |
| 33 | Mexican Bean Beetle (MBB) | 5 | 3 | 1 | 0 | 0 | 0 |
| | Bean Aphid (BA) | — | 5 | 5 | 5 | 5 | 5 |
| 34 | Mexican Bean Beetle (MBB) | 5 | 3 | 2 | 2 | 0 | 0 |
| | Bean Aphid (BA) | — | 5 | 5 | 5 | 4 | 4 |
| 35 | Mexican Bean Beetle (MBB) | 4 | 0 | 0 | 0 | 0 | 0 |
| | Bean Aphid (BA) | 5 | 5 | 5 | 4 | 2 | 1 |
| 36 | Bean Aphid (BA) | 5 | 5 | 3 | 1 | 0 | 0 |
| | Two-Spotted Mite (TSM) | 5 | 5 | 4 | 4 | 3 | 1 |
| 37 | Bean Aphid (BA) | 5 | 5 | 5 | 5 | 4 | 4 |
| | Two-Spotted Mite (TSM) | 4 | 5 | 4 | 1 | 0 | 0 |
| 38 | Mexican Bean Beetle (MBB) | 5 | 5 | 5 | 4 | 1 | 0 |
| | Bean Aphid (BA) | 5 | 5 | 4 | 4 | 4 | 1 |
| | Two-Spotted Mite (TSM) | 5 | 4 | 1 | 0 | 0 | 0 |
| 39 | Mexican Bean Beetle (MBB) | 5 | 5 | 5 | 5 | 5 | 5 |
| | Bean Aphid (BA) | 5 | 5 | 5 | 5 | 5 | 5 |
| | Two-Spotted Mite (TSM) | 5 | 5 | 5 | 5 | 4 | 3 |
| 40 | Mexican Bean Beetle (MBB) | 5 | 5 | 5 | 5 | 5 | 5 |
| | Bean Aphid (BA) | 5 | 5 | 5 | 5 | 5 | 5 |
| | Two-Spotted Mite (TSM) | 5 | 5 | 5 | 4 | 3 | 2 |
| 41 | Mexican Bean Beetle (MBB) | 5 | 5 | 5 | 3 | 2 | 0 |
| | Bean Aphid (BA) | 5 | 5 | 5 | 5 | 4 | 3 |
| | Two-Spotted Mite (TSM) | 4 | 2 | 0 | 0 | 0 | 0 |
| 43 | Bean Aphid (BA) | 4 | 5 | 4 | 4 | 2 | 1 |
| | Two-Spotted Mite (TSM) | 5 | 2 | 0 | 0 | 0 | 0 |
| 44 | Bean Aphid (BA) | 4 | 5 | 5 | 5 | 4 | 3 |
| | Two-Spotted Mite (TSM) | 5 | 0 | 0 | 0 | 0 | 0 |
| 45 | Bean Aphid (BA) | 5 | | | | | |
| | Two-Spotted Mite (TSM) | 2 | | | | | |
| 46 | Mexican Bean Beetle (MBB) | 5 | 4 | 1 | 2 | 0 | 0 |
| | Bean Aphid (BA) | 5 | 5 | 5 | 5 | 5 | 5 |
| | Two-Spotted Mite (TSM) | 5 | 3 | 1 | 0 | 0 | 0 |
| 47 | Bean Aphid (BA) | 5 | 5 | 5 | 4 | 3 | 2 |
| 48 | Bean Aphid (BA) | 3 | 5 | 5 | 4 | 2 | 1 |
| 49 | Mexican Bean Beetle (MBB) | 5 | 5 | 5 | 5 | 4 | 1 |
| | Bean Aphid (BA) | 5 | 5 | 5 | 5 | 5 | 5 |
| 50 | Mexican Bean Beetle (MBB) | 3 | 4 | 5 | 3 | 4 | 1 |
| | Bean Aphid (BA) | 4 | 5 | 5 | 5 | 4 | 4 |
| | Two-Spotted Mite (TSM) | 4 | 5 | 2 | 0 | 0 | 0 |
| 51 | Mexican Bean Beetle (MBB) | 5 | 5 | 5 | 4 | 5 | 3 |
| | Bean Aphid (BA) | 5 | 5 | 5 | 5 | 5 | 5 |
| | Two-Spotted Mite (TSM) | 4 | 4 | 4 | 4 | 4 | 2 |
| 52 | Bean Aphid (BA) | 5 | 4 | 4 | 3 | 2 | 1 |

Method for Southern Corn Rootworm (SCR)

The combating of southern corn rootworms may be demonstrated by means of the following procedure:

Three 5 oz paper cups planted each with one kernel of DeKalb XL-361 corn are treated two days after planting with 10 ml of a 100 ppm solution of the candidate compound. Promising compounds are tested at lower concentrations. The experiment is a 4 × 5 factorial in a randomized complete block design with three replications. The tests are evaluated nine days after treatment. The roots are inspected under a dissecting microscope and rated as follows:

| SCR Rating | % root feeding damage |
|---|---|
| 5 | 0 |
| 4 | 1–25 |
| 3 | 26–50 |
| 2 | 51–75 |
| 1 | 76–99 |
| 0 | 100 |

So as to obtain more meaningful results, all tests are performed at the same time of day, whenever possible, usually in the forenoon. Temperature, illumination and humidity are the same in all tests. Atmospheric pressure is not controlled.

Test results obtained at various concentrations for one of the active chemicals and a commercial insecticide are tabulated below. The ratings given are for averages of three or more replicates.

| CHEMICAL NO. | SPECIES | Conc. ppm 100 | 50 | 25 | 12.5 |
|---|---|---|---|---|---|
| 14 | Southern Corn Rootworm | 5 | 5 | 5 | 5 |
| Furadan | Southern Corn Rootworm | 5 | 5 | 5 | 5 |

For the purposes of this patent "combating insects" means killing or rendering harmless both pestiferous insects and mites and "applying to the locus of insects" means applying on, or near to insects or mites or their eggs or larvae so that there will be contact between the chemical and the organism. "Combating" does not necessarily mean producing a total kill, as it is now known that this may be inadvisable. The survivors of an almost total kill are likely to breed resistant strains, whereas an 80 percent to 90 percent kill will reduce crop damage to an acceptable level without this disadvantage.

It is common and accepted practice to formulate, ship and apply highly toxic insecticides in combination with diluents. By this means, more uniform application of small quantities of insecticides is assured and personal contact with the toxic ingredient at a high concentration level is rendered impossible. In this way a highly toxic substance may be handled with reasonable safety.

Either or both solid and liquid diluents may be employed with the insecticides of this invention. The insecticides may be formulated, for example, as low-concentration dry granules, as liquid emulsifiable concentrates or as emulsifiable powders. Representative procedures are given below. All parts are parts by weight unless otherwise indicated.

Dry Granular Formulation

A slurry of 45 parts of attapulgite clay and 5 grams of insecticide in 80 parts of acetone was prepared. The slurry was then emptied into a rotating drum drying apparatus where the acetone was driven off by a stream of hot air as the drum was rotated. As acetone was removed the slurry became a paste and then a tumbling moist solid mass, after which small pellets or granules began to form. By the time the tumbling mass of solid material was substantially dry it was in the form of 9.4 percent active granules. In granular form the insecticide was particularly useful for combating soil-borne insects.

Wettable Powder

The following ingredients were thoroughly mixed in a blending apparatus in finely divided solid form:

| Insecticide | 10 parts |
|---|---|
| Barden clay | 8 parts |
| Sodium dialkyl-naphthalenesulfonate (75% active; Sellogen HR) | 1 part |
| Sodium-based lignin sulfonate dispersing agent (Polyfon II) | 1 part |

The resulting dry powder was easily dispersed in water to make up liquids for spray application.

Water Dispersible Concentrate

In a solvent mixture containing 257 parts of isophorone and 257 parts of mesityl oxide there was dissolved 40 parts of insecticidal compound, 30 parts of lipophilic emulsifier blend of anionic and nonionic surfactants (T-Mulz O) and 30 parts of a hydrophilic emulsifier blend of anionic and nonionic surfactants (T-Mulz W). The resulting liquid was a 6.5 percent active water-emulsifiable concentrate which was useful for preparing aqueous spray mixtures.

The insecticides of this invention may also be formulated according to conventional methods as oil sprays, microencapsulated powders, thickened aqueous sprays, and may also be incorporated into plasticized polymers to obtain controlled release over prolonged periods of time, as will be understood by skilled workers in the art.

I claim:
1. 3-tert.butyl-1-(N,N-dimethylcarbamyl)-4-methyl-4H-1,2,4-triazoline-5-thione.
2. 1-(N,N-dimethylcarbamyl)-3,4-dimethyl-4H-1,2,4-triazoline-5-thione.
3. 3-tert.butyl-1-(N-methylcarbamyl)-4-methyl-4H-1,2,4-triazoline-5-thione.
4. 1-(N,N-dimethylcarbamyl)-3-isopropyl-4-methyl-4H-1,2,4-triazoline-5-thione.
5. 1-(N,N-diethylcarbamyl)-3-tert. butyl-4-methyl-4H-1,2,4-triazoline-5-thione.
6. 3-Cyclopropyl-1-(N,N-dimethylcarbamyl)-4-methyl-4H-1,2,4-triazoline-5-thione.
7. 1-(N,N-dimethylcarbamyl)-3-ethyl-4-methyl-4H-1,2,4-triazoline-5-thione.
8. 3-tert.butyl-1-(N,N-dimethylcarbamyl)-4-ethyl-4H-1,2,4-triazoline-5-thione.
9. 1-(N,N-dimethylcarbamyl)-4-methyl-3-trifluoromethyl-4H-1,2,4-triazoline-5-thione.
10. 1-(N,N-dimethylcarbamyl)-3-isobutyl-4-methyl-4H-1,2,4-triazoline-5-thione.
11. 3-tert.butyl-1-(N,N-dimethylthiocarbamyl)-4-methyl-4H-1,2,4-triazoline-5-thione.
12. 1-(N,N-dimethylcarbamyl)-3-propenyl-4-methyl-4H-1,2,4-triazoline-5-thione.
13. 1-(N,N-dimethylcarbamyl)-3-cyclohexyl-4-methyl-4H-1,2,4-triazoline-5-thione.

14. 1-(N,N-dimethylcarbamyl)-3-tert.butyl-4-phenyl-4H-1,2,4-triazoline-5-thione.

15. 1-(N,N-dimethylcarbamyl)-3-tert.butyl-4-benzyl-4H-1,2,4-triazoline-5-thione.

16. 1-(N,N-dimethylcarbamyl)-3-cyanomethyl-4-methyl-4H-1,2,4-triazoline-5-thione.

17. 1-(N,N-dimethylcarbamyl)-3-tert.butyl-4-butyl-4H-1,2,4-triazoline-5-thione.

18. 1-(N,N-dimethylcarbamyl)-3-tert.butyl-4-allyl-4H-1,2,4-triazoline-5-thione.

19. 1-(N,N-dimethylcarbamyl)-3-trifluoromethyl-4-ethyl-4H-1,2,4-triazoline-5-thione.

20. 1-(N,N-dimethylcarbamyl)-3-trifluoromethyl-4-allyl-4H-1,2,4-triazoline-5-thione.

21. 1-(N,N-dimethylcarbamyl)-3-trifluoromethyl-4-butyl-4H-1,2,4-triazoline-5-thione.

22. 1-(N,N-dimethylcarbamyl)-3-(p-nitrophenyl)-4-methyl-4H-1,2,4-triazoline-5-thione.

23. 1-(N,N-dimethylcarbamyl)-3-dimethylaminomethyl-4-methyl-4H-1,2,4-triazoline-5-thione.

24. 1-(N,N-dimethylcarbamyl)-3-chlorodifluoromethyl-4-methyl-4H-1,2,4-triazoline-5-thione.

25. 1-(N,N-dimethylcarbamyl)-3-(1,1-dimethylpropyl)-4-methyl-4H-1,2,4-triazoline-5-thione.

26. 1-(N,N-dimethylcarbamyl)-3-(2-methylthioisopropyl)-4-methyl-4H-1,2,4-triazoline-5-thione.

27. 1-(N,N-dimethylcarbamyl)-3-isopropylthio-4-methyl-4H-1,2,4-triazoline-5-thione.

28. 1-(N,N-dimethylcarbamyl)-3-ethylthio-4-methyl-4H-1,2,4-triazoline-5-thione.

29. 1-(N-methylcarbamyl)-3-(1,1-dimethylpropyl)-4-methyl-4H-1,2,4-triazolin-5-one.

30. 1-(N,N-dimethylcarbamyl)-3-isopropylthio-4-methyl-4H-1,2,4-triazolin-5-one.

31. 1-(N,N-dimethylcarbamyl)-3-ethylthio-4-methyl-4H-1,2,4-triazolin-5-one.

32. 1-(N,N-dimethylcarbamyl)-3-methythio-4-methyl-4H-1,2,4-triazolin-5-one.

33. 1-(N,N-dimethylcarbamyl)-3-diethylaminomethyl-4-methyl-4H-1,2,4-triazoline-5-thione.

34. 1-(N,N-dimethylcarbamyl)-3-propylthio-4-methyl-4H-1,2,4-triazoline-5-thione.

35. 1-(N,N-dimethylcarbamyl)-3-allylthio-4-methyl-4H-1,2,4-triazoline-5-thione.

36. 1-(N,N-dimethylcarbamyl)-3-(1-methylpropyl)-4-methyl-4H-1,2,4-triazoline-5-thione.

* * * * *